(12) United States Patent
Kusakabe et al.

(10) Patent No.: US 8,841,478 B2
(45) Date of Patent: Sep. 23, 2014

(54) METHOD FOR PREPARING TRANS-{4-[(ALKYLAMINO) METHYL]-CYCLOHEXYL}ACETIC ACID ESTER

(75) Inventors: Taichi Kusakabe, Chiba (JP); Koichi Yamazaki, Tokyo (JP); Tadaaki Ohgiya, Saitama (JP); Kimiyuki Shibuya, Saitama (JP)

(73) Assignee: Kowa Company, Ltd., Aichi (JP)

( * ) Notice: Subject to any disclaimer, the term of this patent is extended or adjusted under 35 U.S.C. 154(b) by 784 days.

(21) Appl. No.: 13/131,767

(22) PCT Filed: Nov. 27, 2009

(86) PCT No.: PCT/JP2009/006414
§ 371 (c)(1),
(2), (4) Date: Aug. 15, 2011

(87) PCT Pub. No.: WO2010/061621
PCT Pub. Date: Jun. 3, 2010

(65) Prior Publication Data
US 2011/0288328 A1    Nov. 24, 2011

(30) Foreign Application Priority Data
Nov. 28, 2008    (JP) .................................. 2008-303547

(51) Int. Cl.
C07C 233/48 (2006.01)
C07C 227/16 (2006.01)
C07C 231/12 (2006.01)
C07C 231/02 (2006.01)

(52) U.S. Cl.
CPC ........... *C07C 227/16* (2013.01); *C07C 2101/14* (2013.01); *C07C 231/02* (2013.01); *C07C 233/48* (2013.01); *C07C 231/12* (2013.01)
USPC ........................................................ 560/125

(58) Field of Classification Search
CPC .. C07C 233/48; C07C 227/16; C07C 231/12; C07C 231/02
USPC ........................................................ 560/125
See application file for complete search history.

(56) References Cited

U.S. PATENT DOCUMENTS

| | | |
|---|---|---|
| 2005/0059810 A1 | 3/2005 | Maeda et al. |
| 2008/0146620 A1 | 6/2008 | Maeda et al. |
| 2009/0075968 A1 | 3/2009 | Sakaki et al. |
| 2009/0075979 A1 | 3/2009 | Ali et al. |
| 2011/0166351 A1 | 7/2011 | Yamazaki et al. |

FOREIGN PATENT DOCUMENTS

| | | |
|---|---|---|
| WO | 2004/020393 | 3/2004 |
| WO | 2007/073934 | 7/2007 |
| WO | 2007/081571 | 7/2007 |
| WO | 2007/088996 | 8/2007 |
| WO | 2007/128568 | 11/2007 |
| WO | 2008/129951 | 10/2008 |

OTHER PUBLICATIONS

International Search Report for PCT/JP2009/006414, mailed Feb. 16, 2010.
International Preliminary Report on Patentability for PCT/JP2009/006414, mailed Jun. 9, 2011 (along with an English language translation thereof).
Extended European Search report issued with respect to patent family member European Patent App. No. 09828871.5, dated Jul. 5, 2012.

*Primary Examiner* — Yevegeny Valenrod
(74) *Attorney, Agent, or Firm* — Greenblum & Bernstein, P.L.C.

(57) ABSTRACT

A method for preparing a trans-{4-[(alkylamino)methyl] cyclohexyl}acetic acid, which is useful as a raw material compound for manufacture of medicaments and the like, comprising the step of reducing amide group of a compound represented by the following general formula (6) ($R^1$ represents hydrogen atom or a $C_{1-6}$ alkyl group, and $R^2$ represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group).

(6)

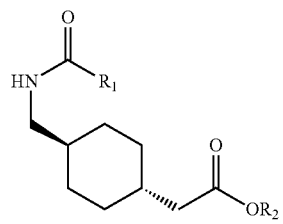

13 Claims, No Drawings

METHOD FOR PREPARING TRANS-{4-[(ALKYLAMINO) METHYL]-CYCLOHEXYL}ACETIC ACID ESTER

TECHNICAL FIELD

The present invention relates to a method for producing a trans-{4-[(alkylamino)methyl]cyclohexyl}acetic acid ester, which is useful as a raw material compound for manufacture of medicaments, agricultural chemicals, and industrial products, and also relates to an intermediate for preparation thereof.

BACKGROUND ART

Trans-{4-[(alkylamino)methyl]cyclohexyl}acetic acid esters are useful as reagents or raw material compounds for manufacture of medicaments, agricultural chemicals, and industrial products. For example, in each of the following publications (Patent documents 1 to 6), trans-{4-[(alkylamino)methyl]cyclohexyl}-acetic acid esters are described as important raw material compounds for preparation of: trans-[4-({[2-({[3,5-bis(trifluoromethyl)benzyl](2-methyl-2H-tetrazol-5-yl)amino}methyl)-5-methyl-4-(trifluoromethyl)phenyl](ethyl)amino}-methyl)cyclohexyl]acetic acid hydrochloride represented by the following formula (A) (Patent document 1, Example 142), trans-[4-({[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino}methyl)cyclohexyl]acetic acid represented by the following formula (B) (Patent document 2, Ex. 73), trans-[4-({[2-({[3,5-bis(trifluoromethyl)benzyl](5-morpholinopyrimidin-2-yl)amino}methyl)-4-(trifluoromethyl)phenyl](ethyl)amino}methyl)cyclohexyl]acetic acid represented by the following formula (C) (Patent document 3, Ex. 57), trans-[4-({[3-({[3,5-bis(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid represented by the following formula (D) (Patent document 4, Ex. 14), trans-[4-({[3-({[3,5-bis(trifluoromethyl)benzyl](2-methyl-2H-tetrazol-5-yl)amino}methyl)quinolin-2-yl](ethyl)amino}methyl)cyclohexyl]acetic acid represented by the following formula (E) (Patent document 5, Ex. 4), trans-(4-{[{2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino]methyl}cyclohexyl)acetic acid represented by the following formula (F) (Patent document 6, Example 45) and the like, which are pyrimidine compounds having a dibenzylamine structure having a cholesterol ester transfer protein (CETP) inhibitory activity and are useful as prophylactic and/or therapeutic agents for hyperlipidemia, arteriosclerosis, heart diseases and the like.

[Formula 1]

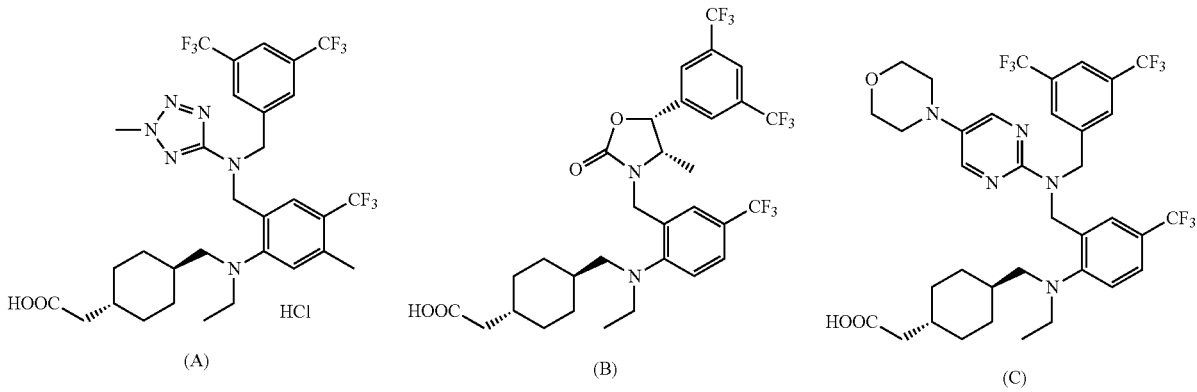

(A)        (B)        (C)

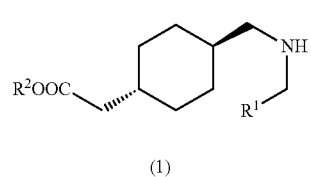

(1)

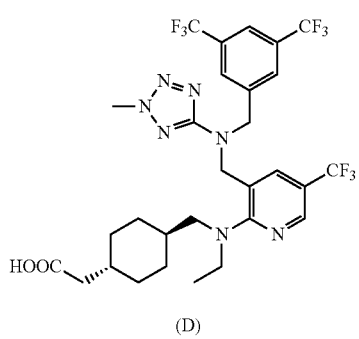

(D)

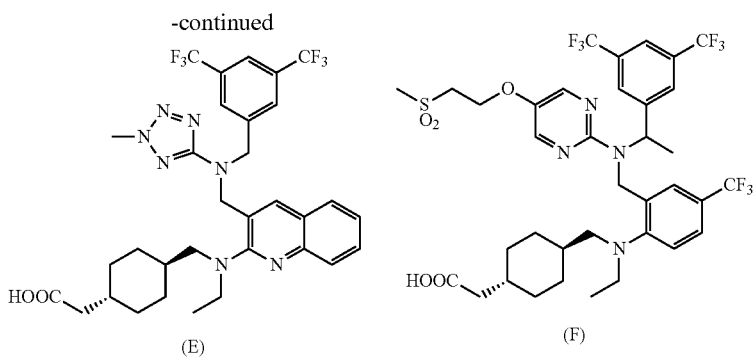

(E)                    (F)

As a method for preparing a trans-{4-[(ethylamino)methyl]cyclohexyl}acetic acid ester, the method shown in the following reaction scheme is known. This method uses 4-oxocyclohexanecarboxylic acid ethyl ester as a starting material, and comprises the steps of derivatizing the starting material to obtain the cyclohexylacetic acid compound by a carbon increasing reaction based on the Horner-Wittig-Emmons reaction, reducing the double bond of the unsaturated ester of the cyclohexylacetic acid compound to obtain the cyclohexylcarboxylic acid compound as a mixture of the compounds of cis- and trans-configurations, then converting the resulting cyclohexylcarboxylic acid into the acid chloride without separating the isomers, and then converting the acid chloride into the amide compound by a reaction with ethylamine. The desired amide compound having the trans-configuration can be separated by repeating recrystallization several times. The resulting amide compound can be reduced with sodium borohydride in the presence of acetic acid to obtain a trans-{4-[(ethylamino)methyl]cyclohexyl}acetic acid ester, which is an amine compound (refer to Patent document 1, Example 169).

Reaction Route 1

[Formula 2]

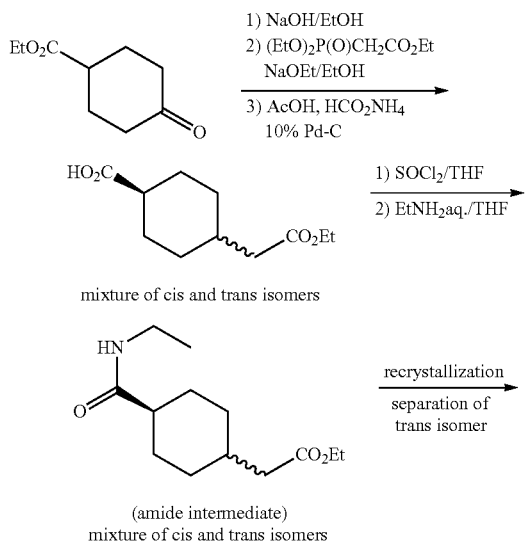

mixture of cis and trans isomers (amide intermediate)
mixture of cis and trans isomers

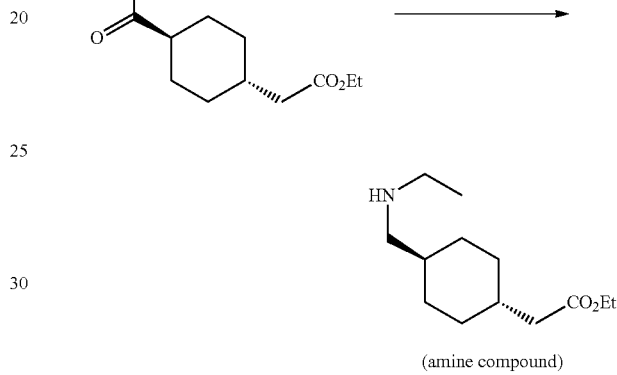

(amine compound)

However, the operations of the aforementioned method are complicated, since the desired amide intermediate having the trans-configuration is separated and purified from a mixture of the cis- and trans-isomers by recrystallization, and thus the total yield is also low (32.2%). Further, it is difficult to carry out the conversion of the non-desired cis-compound into the trans-compound by an ordinary method, and therefore, the method also suffers from a problem that the cis-compound cannot be recycled. Furthermore, the 4-oxocyclohexanecarboxylic acid ethyl ester as the starting material is not inexpensive at present, and therefore the method cannot be regarded as an industrially efficient and advantageous preparation method.

In order to avoid loss in a yield due to the separation by recrystallization, a method has been proposed in which the cyclohexylacetic acid, obtained by the carbon increasing reaction based on the Horner-Wittig-Emmons reaction and the successive reduction, is derived into a benzyl ester intermediate so as to facilitate the separation of the cis- and trans-isomers. After separation and purification of the mixture of the isomers is carried out by column chromatography to obtain the cyclohexylacetic acid derivative of the trans-configuration, the target compound can be obtained by steps similar to those of the aforementioned method (see, Intermediate 7 and Intermediate 13 of Patent document 2). This reaction route is shown with reaction formulas as follows.

Reaction Route 2

[Formula 3]

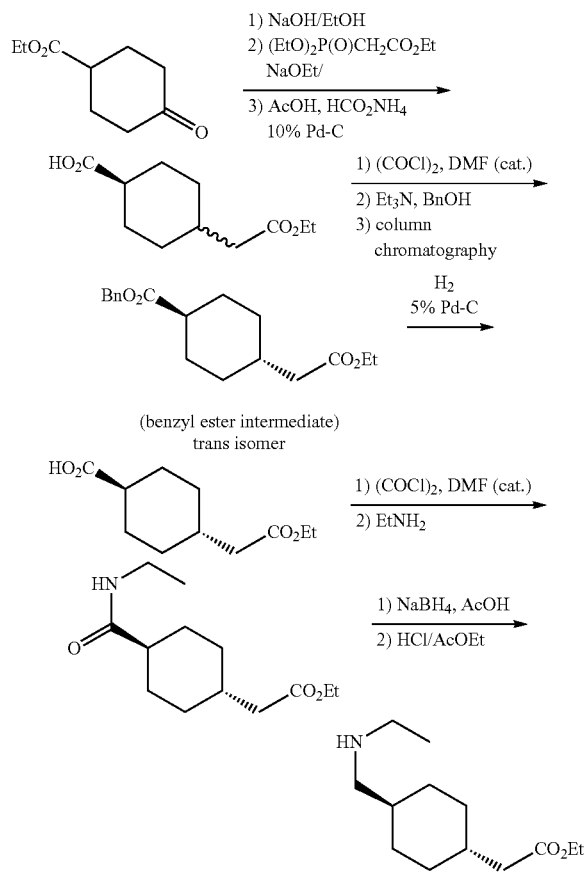

However, this method additionally comprises the steps of converting the carboxylic acid into the benzyl ester intermediate for the separation by column chromatography and, after separating the desired objective substance, converting the benzyl ester into a carboxylic acid by hydrogenolysis. Therefore, an yield may possibly be reduced significantly due to the separation of the isomers. Further, the operations of the column chromatography for the separation of the isomers are complicated, and accordingly, the method is considered not to be efficient preparation method from an industrial viewpoint.

PRIOR ART REFERENCES

Patent Documents

Patent document 1: International Patent Publication WO2004/020393
Patent document 2: International Patent Publication WO2007/081571
Patent document 3: International Patent Publication WO2007/088996
Patent document 4: International Patent Publication WO2007/073934
Patent document 5: International Patent Publication WO2007/128568
Patent document 6: International Patent Publication WO2008/129951

SUMMARY OF THE INVENTION

Object to be Achieved by the Invention

An object of the present invention is to provide a method for efficiently preparing a trans-{4-[(alkylamino)methyl]cyclohexyl}acetic acid ester, which is useful as a reagent or a starting material compound for manufacture of medicaments, agricultural chemicals, industrial products and the like, from an inexpensive raw material compound in a high yield.

Another object of the present invention is to provide a novel preparation intermediate useful for efficiently preparing a trans-{4-[(alkylamino)methyl]-cyclohexyl}acetic acid ester from an inexpensive raw material compound in a high yield.

Means for Achieving the Object

The inventors of the present invention conducted various researches to achieve the aforementioned objects, and as a result, they found that, as shown in the following reaction scheme, by using inexpensively available tranexamic acid (2) having the trans-configuration as a starting material, and converting tranexamic acid into an amide compound (3) by acylation, then converting the carboxylic acid into a compound (4) using a halogenating agent or an active esterifying agent, and further converting the compound (4) into a diazoketone compound (5) through a reaction with diazomethane or trimethylsilyldiazomethane, and then subjecting the diazoketone compound (5) to the Arndt-Eistert reaction in an alcohol solution in the presence of a silver salt and a tertiary amine, conversion into a novel ester compound (6) was efficiently achievable, of which carbon number was increased by one with while the trans-configuration was maintained. Further, they also found that the desired trans-{4-[(alkylamino)methyl]cyclohexyl}acetic acid ester (1) was successfully obtained in a excellent yield by reduction of the amide of the ester compound (6) in a conventional manner. The present invention was accomplished on the basis of the aforementioned findings.

[Formula 4]

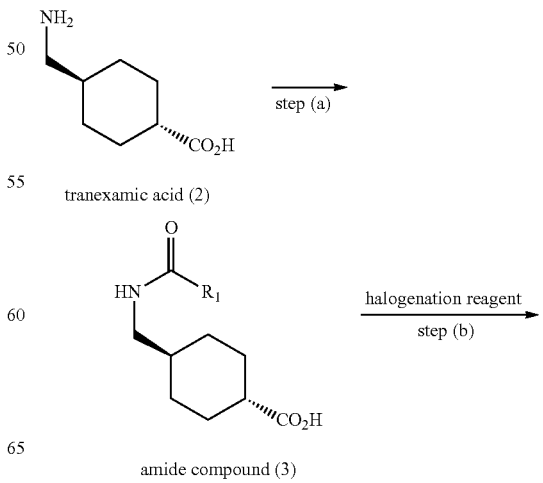

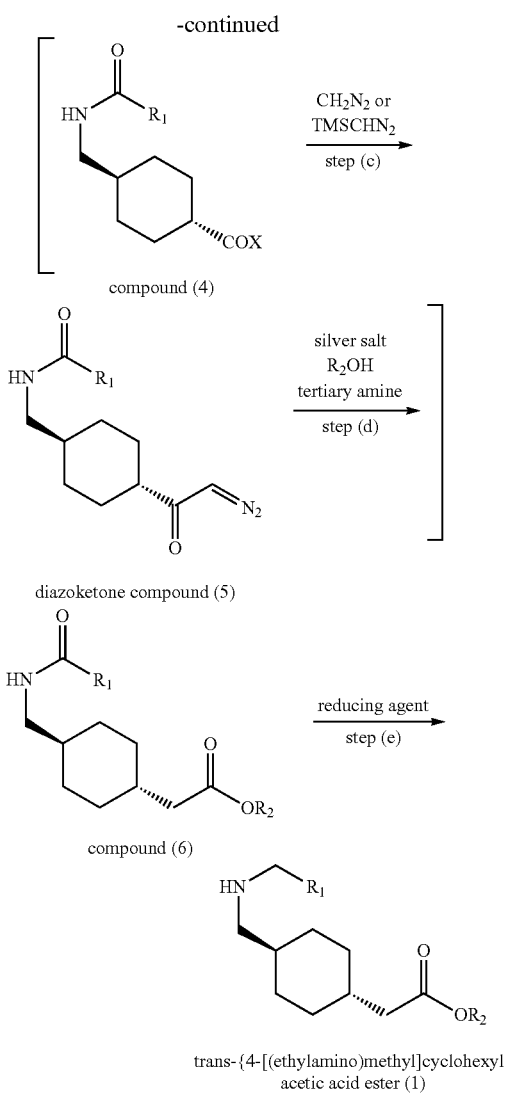

[In the formula, $R^1$ represents hydrogen atom or a $C_{1-6}$ alkyl group, $R^2$ represents a $C_{1-6}$ alkyl group, a $C_{3-6}$ cycloalkyl group, a $(C_{3-6}$ cycloalkyl$)(C_{1-6}$ alkyl$)$ group, a $C_{6-10}$ aryl group, or a $C_{7-12}$ aralkyl group, and X represents a halogen atom or an active ester residue.]

The present invention thus provides a method for preparing a trans-{4-[(alkylamino)methyl]cyclohexyl}acetic acid ester represented by the aforementioned general formula (1) (in the formula, $R^1$ represents hydrogen atom or a $C_{1-6}$ alkyl group, and $R^2$ represents a $C_{1-6}$ alkyl group, a $C_{3-6}$ cycloalkyl group, a $(C_{3-6}$ cycloalkyl$)(C_{1-6}$ alkyl$)$ group, a $C_{6-10}$ aryl group, or a $C_{7-12}$ aralkyl group), which comprises the step of reducing amide group of a compound represented by the aforementioned general formula (6) ($R^1$ and $R^2$ in the formula have the same meanings as those defined above). According to preferred embodiments of the present invention, there are provided the aforementioned method, wherein sodium borohydride is used as a reducing agent, and the aforementioned method, wherein $R^1$ is methyl group.

The compound represented by the aforementioned general formula (6) used in the aforementioned method of the present invention is a novel compound, and this compound is useful as a preparation intermediate of a trans-{4-[(alkylamino)-methyl]cyclohexyl}acetic acid ester represented by the aforementioned general formula (1).

Therefore, from further aspects, the present invention provides a compound represented by the aforementioned general formula (6) ($R^1$ and $R^2$ in the formula have the same meanings as those defined above), and a compound represented by the aforementioned general formula (6) for use as an intermediate for preparation of a trans-{4-[(alkylamino)methyl] cyclohexyl}acetic acid ester represented by the aforementioned general formula (1). In the compound represented by the aforementioned general formula (6), $R^1$ is preferably methyl group.

The present invention further provides a method for preparing a compound represented by the aforementioned general formula (6) ($R^1$ and $R^2$ in the formula have the same meanings as those defined above), which comprises the step of reacting a compound represented by the aforementioned general formula (5) ($R^1$ in the formula has the same meaning as that defined above) with an alcohol compound represented as $R^2$—OH ($R^2$ in the formula has the same meanings as that defined above) in the presence of a silver salt and a tertiary amine.

The present invention also provides a method for preparing a compound represented by the aforementioned general formula (6) ($R^1$ and $R^2$ in the formula have the same meanings as those defined above), which comprises the step of reacting a compound represented by the aforementioned general formula (4) ($R^1$ in the formula has the same meaning as that defined above, and X represents a halogen atom or an active ester residue) with diazomethane or trimethylsilyldiazomethane to prepare a compound represented by the aforementioned general formula (5) ($R^1$ in the formula has the same meaning as that defined above); and the step of reacting the resulting compound represented by the aforementioned general formula (5) ($R^1$ in the formula has the same meaning as that defined above) with an alcohol compound represented as $R^2$—OH ($R^2$ in the formula has the same meanings as that defined above) in the presence of a silver salt and a tertiary amine, and a method for preparing a compound represented by the aforementioned general formula (6) ($R^1$ and $R^2$ in the formula have the same meanings as those defined above), which comprises the step of reacting a compound represented by the aforementioned general formula (3) ($R^1$ in the formula has the same meaning as that defined above) with a halogenating agent or an active esterifying agent to prepare a compound represented by the aforementioned general formula (4) ($R^1$ in the formula has the same meaning as that defined above, and X represents a halogen atom or an active ester residue); the step of reacting the resulting compound represented by the aforementioned general formula (4) with diazomethane or trimethylsilyldiazomethane to prepare a compound represented by the aforementioned general formula (5) ($R^1$ in the formula has the same meaning as that defined above); and the step of reacting the resulting compound represented by the aforementioned general formula (5) ($R^1$ in the formula has the same meaning as that defined above) with an alcohol compound represented as $R^2$—OH ($R^2$ in the formula has the same meanings as that defined above) in the presence of a silver salt and a tertiary amine.

The present invention further provides a method for preparing a compound represented by the aforementioned general formula (6) ($R^1$ and $R^2$ in the formula have the same meanings as those defined above), which comprises the step of acylating tranexamic acid (2) to prepare a compound represented by the aforementioned general formula (3) ($R^1$ in the formula has the same meaning as that defined above); the step of reacting the resulting compound represented by the aforementioned general formula (3) ($R^1$ in the formula has the same meaning as that defined above) with a halogenating agent or an active esterifying agent to prepare a compound represented by the aforementioned general formula (4) ($R^1$ in the formula has the same meaning as that defined above, and X represents a halogen atom or an active ester residue); the step of reacting the resulting compound represented by the aforementioned general formula (4) with diazomethane or trimethylsilyldiazomethane to prepare a compound represented by the aforementioned general formula (5) ($R^1$ in the formula has the same meaning as that defined above); and the step of reacting the resulting compound represented by the aforementioned general formula (5) ($R^1$ in the formula has the same meaning as that defined above) with an alcohol compound represented as $R^2$—OH ($R^2$ in the formula has the same meaning as that defined above) in the presence of a silver salt and a tertiary amine.

In addition to these methods, the present invention also provides a method for preparing a trans-{4-[(alkylamino) methyl]cyclohexyl}acetic acid ester represented by the aforementioned general formula (1) (in the formula, $R^1$ and $R^2$ have the same meanings as those defined above), which comprises:

(a) the step of acylating tranexamic acid (2) to prepare a compound represented by the aforementioned general formula (3) ($R^1$ in the formula has the same meaning as that defined above);
(b) the step of reacting the compound represented by the aforementioned general formula (3) ($R^1$ in the formula has the same meaning as that defined above) obtained in the aforementioned step (a) with a halogenating agent or an active esterifying agent to prepare a compound represented by the aforementioned general formula (4) ($R^1$ in the formula has the same meaning as that defined above, and X represents a halogen atom or an active ester residue);
(c) the step of reacting the compound represented by the aforementioned general formula (4) obtained in the aforementioned step (b) with diazomethane or trimethylsilyldiazomethane to prepare a compound represented by the aforementioned general formula (5) ($R^1$ in the formula has the same meaning as that defined above);
(d) the step of reacting the compound represented by the aforementioned general formula (5) ($R^1$ in the formula has the same meaning as that defined above) obtained in the aforementioned step (c) with an alcohol compound represented as $R^2$—OH ($R^2$ in the formula has the same meaning as that defined above) in the presence of a silver salt and a tertiary amine to prepare a compound represented by the aforementioned general formula (6) ($R^1$ and $R^2$ in the formula have the same meanings as those defined above); and
(e) the step of reducing amide group of the compound represented by the aforementioned general formula (6) ($R^1$ and $R^2$ in the formula have the same meanings as those defined above) obtained in the aforementioned step (d), and a method for preparing a trans-{4-[(alkylamino)methyl] cyclohexyl}acetic acid ester represented by the aforementioned general formula (1) (in the formula, $R^1$ and $R^2$ have the same meanings as those defined above), which comprises one or more steps selected from the group consisting of the aforementioned steps (a) to (e).

Effect of the Invention

According to the method of the present invention, a trans-{4-[(alkylamino)-methyl]cyclohexyl}acetic acid ester, which is useful as a reagent or a raw material compound for manufacture of medicaments, agricultural chemicals, industrial products and the like, can be efficiently prepared from an inexpensive raw material compound in a high yield. This method is especially advantageous for reducing manufacturing cost and improving manufacturing efficiency from an industrial viewpoint.

The novel compound represented by aforementioned general formula (6) provided by the present invention is useful as a preparation intermediate for efficiently preparing the aforementioned trans-{4-[(alkylamino)methyl]-cyclohexyl}acetic acid ester in a high yield.

MODES FOR CARRYING OUT THE INVENTION

In the present invention, the $C_{1-6}$ alkyl group means to a linear or branched alkyl group having 1 to 6 carbon atoms, and examples include, for example, methyl group, ethyl group, propyl group, isopropyl group, butyl group, isobutyl group, s-butyl group, t-butyl group, pentyl group, hexyl group, and the like.

In the present invention, the $C_{3-6}$ cycloalkyl group means a cyclic alkyl group having 3 to 6 carbon atoms, and examples include, for example, cyclopropyl group, cyclobutyl group, cyclopentyl group, cyclohexyl group, and the like.

In the present invention, the ($C_{3-6}$ cycloalkyl)($C_{1-6}$ alkyl) group means a linear or branched $C_{1-6}$ alkyl group substituted with a cyclic $C_{3-6}$ alkyl group, and examples include, for example, cyclopropylmethyl group, cyclopropylethyl group, cyclopropylpropyl group, cyclobutylmethyl group, cyclobutylethyl group, cyclobutylpropyl group, cyclopentylmethyl group, cyclopentylethyl group, cyclopentylpropyl group, cyclohexylmethyl group, cyclohexylethyl group, cyclohexylpropyl group, and the like.

In the present invention, the $C_{6-10}$ aryl group means an aromatic hydrocarbon group having 6 to 10 carbon atoms, and examples include, for example, phenyl group, naphthyl group, azulenyl group, and the like.

In the present invention, the $C_{7-12}$ aralkyl group means a $C_{1-6}$ alkyl group substituted with phenyl group, and examples include, for example, benzyl group, phenethyl group, phenylpropyl group, phenylbutyl group, phenylpentyl group, phenylhexyl group, and the like.

In the present invention, examples of the active ester residue include, for example, phenoxy group, p-nitrophenoxy group, 1,3,5-trichlorophenoxy group, pentafluorophenoxy group, 2,4-dinitrophenoxy group, (pyridin-2-yl)oxy group, an ester residue derived from N-hydroxysuccinimide, an ester residue derived from N-hydroxypiperidine, an ester residue derived from N-hydroxy-5-norbornene-2,3-dicarboxylic acid imide, an ester residue derived from 8-hydroxyquinoline, and the like.

It is clearly understood that the trans-{4-[(alkylamino)methyl]cyclohexyl}-acetic acid esters prepared by the method of the present invention are useful as reagents or raw material compounds for manufacture of various medicaments, agricultural chemicals, industrial products and the like in view of the fact, for example, that they are used as preparation raw material in Example 142 of Patent document 1, Example 73 of Patent document 2, Example 57 of Patent document 3, Example 14 of Patent document 4, Example 4 of Patent document 5, Example 45 of Patent document 6, and the like.

Specifically, examples of the trans-{4-[(alkylamino)methyl]cyclohexyl}acetic acid ester include, for example, trans-[4-({[6-({[3,5-bis(trifluoromethyl)benzyl](2-methyl-2H-tetrazol-5-yl)amino}methyl)indan-5-yl](ethyl)amino}methyl) cyclohexyl]acetic acid hydrochloride (Patent document 1, Example 111), trans-[4-({[2-({[3,5-bis(trifluoromethyl)benzyl](2-methyl-2H-tetrazol-5-yl)amino}methyl)-4-(trifluoromethoxy)phenyl](ethyl)amino}methyl)cyclohexyl]acetic acid hydrochloride (Patent document 1, Example 115), trans-[4-({[2-({[3,5-bis(trifluoromethyl)benzyl](2-methyl-2H-tetrazol-5-yl)amino}methyl)-4-(trifluoromethyl)phenyl](ethyl)amino}methyl)cyclohexyl]acetic acid hydrochloride (Patent document 1, Example 118), trans-[4-({[6-({[3,5-bis(trifluoromethyl)benzyl](2-methyl-2H-tetrazol-5-yl)amino}methyl)-2,2-difluoro-1,3-benzodioxol-5-yl](ethyl)amino}methyl)cyclohexyl]acetic acid hydrochloride (Patent document 1, Example 134), trans-[4-({[7-({[3,5-bis(trifluoromethyl)benzyl](2-methyl-2H-tetrazol-5-yl)amino}methyl)-2,2,3,3-tetrafluoro-2,3-dihydro-1,4-benzodioxin-6-yl](ethyl)amino}methyl)cyclohexyl]acetic acid hydrochloride (Patent document 1, Example 137), trans-[4-({[2-({[3,5-bis(trifluoromethyl)benzyl](2-methyl-2H-tetrazol-5-yl)amino}methyl)-5-methyl-4-(trifluoromethyl)phenyl](ethyl)amino}methyl)cyclohexyl]acetic acid hydrochloride (Patent document 1, Example 142), trans-[4-({[2-({[3,5-bis(trifluoromethyl)benzyl](2-methyl-2H-tetrazol-5-yl)amino}methyl)-4-methyl-5-(trifluoromethyl)phenyl](ethyl)amino}methyl)cyclohexyl]acetic acid hydrochloride (Patent document 1, Example 143), trans-[4-({[2-({[3,5-bis(trifluoromethyl)benzyl](2-methyl-2H-tetrazol-5-yl)amino}methyl)-4-bromophenyl](ethyl)amino}methyl)cyclohexyl]acetic acid hydrochloride (Patent document 1, Example 147), trans-[4-({[2-({[3,5-bis(trifluoromethyl)benzyl](2-methyl-2H-tetrazol-5-yl)amino}methyl)-4,5-dimethylphenyl](ethyl)amino}methyl)cyclohexyl]acetic acid hydrochloride (Patent document 1, Example 151), trans-[4-({[2-({[3,5-bis(trifluoromethyl)benzyl](2-methyl-2H-tetrazol-5-yl)amino}methyl)-4-(trifluoromethylthio)phenyl](ethyl)amino}methyl)cyclohexyl]acetic acid hydrochloride (Patent document 1, Example 152), trans-[4-({[2-({[3,5-bis(trifluoromethyl)benzyl](2-methyl-2,1-tetrazol-5-yl)amino}methyl)-4-chloro-5-ethylphenyl](ethyl)amino}methyl)cyclohexyl]acetic acid hydrochloride (Patent document 1, Example 153), trans-[4-({[2-({[3,5-bis(trifluoromethyl)benzyl](2-methyl-2H-tetrazol-5-yl)amino}methyl)-4-(trifluoromethyl)phenyl](propyl)amino}methyl)cyclohexyl]acetic acid hydrochloride (Patent document 1, Example 154), trans-[4-({[2-({[3,5-bis(trifluoromethyl)benzyl](2-methyl-2H-tetrazol-5-yl)amino}methyl)-5-methoxy-4-methylphenyl](ethyl)amino}methyl)cyclohexyl]acetic acid hydrochloride (Patent document 1, Example 155), trans-[4-({[2-({[3,5-bis(trifluoromethyl)benzyl](2-methyl-2H-tetrazol-5-yl)amino}methyl)-5-methyl-4-(trifluoromethyl)phenyl](propyl)amino}methyl)cyclohexyl]acetic acid hydrochloride (Patent document 1, Example 157), trans-[4-({[2-({[3,5-bis(trifluoromethyl)benzyl](2-methyl-2H-tetrazol-5-yl)amino}methyl)-4-(trifluoromethoxy)phenyl](propyl)amino}methyl)cyclohexyl]acetic acid hydrochloride (Patent document 1, Example 158), trans-[4-({[2-({[3,5-bis(trifluoromethyl)benzyl](p-tolyl)amino}methyl)-4-(trifluoromethoxy)phenyl](ethyl)amino}methyl)cyclohexyl]acetic acid dihydrochloride (Patent document 1, Example 162), trans-[4-({[2-({[3,5-bis(trifluoromethyl)benzyl](5-methyl-[1,2,4]oxadiazol-3-yl)amino}methyl)-4-(trifluoromethoxy)phenyl](ethyl)amino}methyl)cyclohexyl]acetic acid hydrochloride (Patent document 1, Example 163), trans-[4-({[2-({[3,5-bis(trifluoromethyl)benzyl](5-methyl-[1,2,4]oxadiazol-3-yl)amino}methyl)-5-methyl-4-(trifluoromethyl)phenyl](ethyl)amino}methyl)cyclohexyl]acetic acid hydrochloride (Patent document 1, Example 164), trans-[4-({[2-({[3,5-bis(trifluoromethyl)benzyl](5-methyl-[1,2,4]oxadiazol-3-yl)amino}methyl)-5-methyl-4-(trifluoromethyl)phenyl](propyl)amino}methyl)cyclohexyl]acetic acid hydrochloride (Patent document 1, Example 165), trans-[4-({[2-({[3,5-bis(trifluoromethyl)benzyl](2-methyl-2H-tetrazol-5-yl)amino}methyl)-5-methyl-4-(trifluoromethyl)phenyl](propyl)amino}methyl)cyclohexyl]acetic acid (Patent document 1, Example 166), trans-[4-({[2-({[3,5-bis(trifluoromethyl)benzyl](2-methyl-2H-tetrazol-5-yl)amino}methyl)-4-methyl-5-(trifluoromethyl)phenyl](ethyl)amino}methyl)cyclohexyl]acetic acid (Patent document 1, Example 167), trans-[4-({[2-({[3,5-bis(trifluoromethyl)benzyl](2-methyl-2H-tetrazol-5-yl)amino}methyl)-5-methyl-4-(trifluoromethyl)phenyl](ethyl)amino}methyl)cyclohexyl]acetic acid methanesulfonate (Patent document 1, Example 168), ethyl trans-[4-({[2-({[3,5-bis(trifluoromethyl)benzyl](2-methyl-2H-tetrazol-5-yl)amino}methyl)-5-methyl-4-(trifluoromethyl)phenyl](ethyl)amino}methyl)cyclohexyl]acetate (Patent document 1, Example 169), trans-[4-({[2-({[3,5-bis(trifluoromethyl)benzyl](2-methyl-2H-tetrazol-5-yl)amino}methyl)-5-methyl-4-(trifluoromethyl)phenyl](ethyl)amino}methyl)cyclohexyl]acetic acid (Patent document 1, Example 170), trans-[4-({[2-({[3-methyl-5-(trifluoromethyl)benzyl](2-methyl-2H-tetrazol-5-yl)amino}methyl)-5-methyl-4-(trifluoromethyl)phenyl](ethyl)amino}methyl)cyclohexyl]acetic acid (Patent document 1, Example 171), trans-[4-({[2-({[3-methyl-5-(trifluoromethyl)benzyl](5-methyl-[1,2,4]oxadiazol-3-yl)amino}methyl)-5-methyl-4-(trifluoromethyl)phenyl](ethyl)amino}methyl)cyclohexyl]acetic acid (Patent document 1, Example 172), ethyl trans-[4-({[2-({(4S,5R)-5-[3,5-bis(trifluoromethyl)phenyl]-4-methyl-2-oxo-1,3-oxazolidin-3-yl}methyl)-4-(trifluoromethyl)benzyl](ethyl)amino}methyl)cyclohexyl]acetate (Patent document 2, Ex. 11), trans-[4-({[2-({(4S,5R)-5-[3,5-bis(trifluoromethyl)phenyl]-4-methyl-2-oxo-1,3-oxazolidin-3-yl}methyl)-4-(trifluoromethyl)benzyl](ethyl)amino}methyl)cyclohexyl]acetic acid (Patent document 2, Ex. 13), ethyl trans-[4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino}methyl)cyclohexyl]acetate (Patent document 2, Ex. 34), ethyl trans-[4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl](propyl)amino}methyl)cyclohexyl]acetate (Patent document 2, Ex. 36), trans-[4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino}methyl)cyclohexyl]acetic acid (Patent document 2, Ex. 64), trans-[4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl](propyl)amino}methyl)cyclohexyl]acetic acid (Patent document 2, Ex. 65), trans-[4-({[2-({(4S,5R)-5-[3,5-bis(trifluoromethyl)phenyl]-4-methyl-2-oxo-1,3-oxazolidin-3-yl}methyl)pyridin-3-yl](ethyl)amino}methyl)cyclohexyl]acetic acid (Patent document 2, Ex. 69), trans-[4-({[2-({(4S,5R)-5-[3,5-bis(trifluoromethyl)phenyl]-4-methyl-2-oxo-1,3-oxazolidin-3-yl}methyl)-6-isopropenylpyridin-3-yl](ethyl)amino}methyl)cyclohexyl]acetic acid (Patent document 2, Ex. 70), trans-[4-({[2-({(4S,5R)-5-[3,5-bis(trifluoromethyl)phenyl]-4-methyl-2-oxo-1,3-oxazolidin-3-yl}methyl)-6-isopropylpyridin-3-yl](ethyl)amino}methyl)cyclohexyl]acetic acid (Patent document 2, Ex. 71), trans-[4-({[2-({(4S,5R)-5-[3,5-bis(trifluoromethyl)phenyl]-4-methyl-2-oxo-1,3-oxazolidin-3-yl}methyl)-6-cyclopropylpyridin-3-yl](ethyl)amino}methyl)cyclohexyl]acetic acid (Patent document 2, Ex. 72), trans-[4-({[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino}methyl)cyclohexyl]acetic acid (Patent document 2, Ex. 73), trans-[4-({[2-({[3,5-bis(trifluoromethyl)benzyl]}[5-(2-hydroxyethoxy)pyrimidin-2-yl]amino}methyl)-4-(trifluoromethyl)phenyl](ethyl)amino}methyl)cyclohexyl]acetic acid (Patent document 3, Ex. 13), trans-[4-({[2-({[3,5-bis(trifluoromethyl)benzyl](5-morpholinopyrimidin-2-yl)amino}methyl)-4-(trifluoromethyl)phenyl](ethyl)amino}methyl)cyclohexyl]acetic acid (Patent document 3, Ex. 57), ethyl trans-[4-({[3-({[3,5-bis(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-1), ethyl trans-[4-({ethyl[3-({(2-methyl-2H-tetrazol-5-yl)[3-nitro-5-(trifluoromethyl)benzyl]amino}methyl)-5-(trifluoromethyl)pyridin-2-yl]amino}methyl)cyclohexyl]acetate (Patent document 4, Ex. 5-2), ethyl trans-[4-({[3-({[3-cyano-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-3), ethyl trans-[4-({[3-({[3-chloro-2-fluoro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-4), ethyl trans-[4-({[3-({[3,5-bis(trifluoromethyl)benzyl](phenyl)amino}methyl)-5-(trifluoromethyl)pyridin-2-yl](ethyl)amino}methyl)cyclohexyl]acetate (Patent document 4, Ex. 5-5), ethyl trans-[4-({[3-({[3-chloro-5-(trifluoromethyl)benzyl](phenyl)amino}methyl)-5-(trifluoromethyl)pyridin-2-yl](ethyl)amino}methyl)cyclohexyl]acetate (Patent document 4, Ex. 5-6), ethyl trans-[4-({[3-({[3,5-bis(trifluoromethyl)benzyl](1-methyl-1H-pyrazol-3-yl)amino}methyl)-5-(trifluoromethyl)pyridin-2-yl](ethyl)amino}methyl)cyclohexyl]acetate (Patent document 4, Ex. 5-7), ethyl trans-[4-({[3-({[3-chloro-5-(trifluoromethyl)benzyl](1-methyl-1H-pyrazol-3-yl)amino}methyl)-5-(trifluoromethyl)pyridin-2-yl](ethyl)amino}methyl)cyclohexyl]acetate (Patent document 4, Ex. 5-8), ethyl trans-[4-({[3-({[3,5-bis(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetate (Patent document 4, Ex. 5-9), ethyl trans-[4-({[3-({[3-chloro-5-(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetate (Patent document 4, Ex. 5-10), ethyl trans-[4-({[3-({[3-chloro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-11), ethyl trans-[4-({[3-({[3,5-bis(trifluoromethyl)benzyl](methoxycarbonyl)amino}methyl)-5-(trifluoromethyl)pyridin-2-yl](ethyl)amino}methyl)cyclohexyl]acetate (Patent document 4, Ex. 6-1), ethyl trans-[4-({[3-({N-[3,5-bis(trifluoromethyl)benzyl]acetamido}methyl)-5-(trifluoromethyl)pyridin-2-yl](ethyl)amino}methyl)cyclohexyl]acetate (Patent document 4, Ex. 6-2), ethyl trans-[4-({[3-({1-[3,5-bis(trifluoromethyl)benzyl]-3,3-dimethylureido}methyl)-5-(trifluoromethyl)pyridin-2-yl](ethyl)amino}methyl)cyclohexyl]acetate (Patent document 4, Ex. 6-3), ethyl trans-[4-({[3-({N-[3,5-bis(trifluoromethyl)benzyl]methylsulfonamido}methyl)-5-(trifluoromethyl)pyridin-2-yl](ethyl)amino}methyl)cyclohexyl]acetate (Patent document 4, Ex. 6-4), ethyl trans-[4-({[3-({[3,5-bis(trifluoromethyl)benzyl](2-methyl-2H-tetrazol-5-yl)amino}methyl)-5-phenylpyridin-2-yl](ethyl)amino}methyl)cyclohexyl]acetate (Patent document 4, Ex. 7), ethyl trans-[4-({[5-({[3,5-bis(trifluoromethyl)benzyl](2-methyl-2H-tetrazol-5-yl)amino}methyl)-3,3'-bipyridin-6-yl](ethyl)amino}methyl)cyclohexyl]acetate (Patent document 4, Ex. 8-1), ethyl trans-[4-({[3-({[3,5-bis(trifluoromethyl)benzyl](2-methyl-2H-tetrazol-5-yl)amino}methyl)-5-chloropyridin-2-yl](ethyl)amino}methyl)cyclohexyl]acetate (Patent document 4, Ex. 13-1), ethyl trans-[4-({[3-({[3,5-bis(trifluoromethyl)benzyl](2-methyl-2H-tetrazol-5-yl)amino}methyl)-5-bromopyridin-2-yl](ethyl)amino}methyl)cyclohexyl]acetate (Patent document 4, Ex. 13-2), trans-[4-({[3-({[3,5-bis(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 14), trans-[4-({[3-({[3-chloro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 15-1), trans-[4-({ethyl[3-({(2-methyl-2H-tetrazol-5-yl)[3-nitro-5-(trifluoromethyl)benzyl]amino}methyl)-5-(trifluoromethyl)pyridin-2-yl]amino}methyl)cyclohexyl]acetic acid (Patent document 4, Ex. 15-2), trans-[4-({[3-({[3-cyano-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 15-3), trans-[4-({[3-({[3-chloro-2-fluoro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 15-4), trans-[4-({[3-({[3,5-bis(trifluoromethyl)benzyl](phenyl)amino}methyl)-5-(trifluoromethyl)pyridin-2-yl](ethyl)amino}methyl)cyclohexyl]acetic acid (Patent document 4, Ex. 15-5), trans-[4-({[3-({[3-chloro-5-(trifluoromethyl)benzyl](phenyl)amino}methyl)-5-(trifluoromethyl)pyridin-2-yl](ethyl)amino}methyl)cyclohexyl]acetic acid (Patent document 4, Ex. 15-6), trans-[4-({[3-({[3,5-bis(trifluoromethyl)benzyl](methoxycarbonyl)amino}methyl)-5-(trifluoromethyl)pyridin-2-yl](ethyl)amino}methyl)cyclohexyl]acetic acid (Patent document 4, Ex. 15-7), trans-[4-({[3-({N-[3,5-bis(trifluoromethyl)benzyl]acetamido}methyl)-5-(trifluoromethyl)pyridin-2-yl](ethyl)amino}methyl)cyclohexyl]acetic acid (Patent document 4, Ex. 15-8), trans-[4-({[3-({1-[3,5-bis(trifluoromethyl)benzyl]-3,3-dimethylureido}methyl)-5-(trifluoromethyl)pyridin-2-yl](ethyl)amino}methyl)cyclohexyl]acetic acid (Patent document 4, Ex. 15-9), trans-[4-({[3-({N-[3,5-bis(trifluoromethyl)benzyl]methylsulfonamido}methyl)-5-(trifluoromethyl)pyridin-2-yl](ethyl)amino}methyl)cyclohexyl]acetic acid (Patent document 4, Ex. 15-10), trans-[4-({[3-({[3,5-bis(trifluoromethyl)benzyl](1-methyl-1H-pyrazol-3-yl)amino}methyl)-5-(trifluoromethyl)pyridin-2-yl](ethyl)amino}methyl)cyclohexyl]acetic acid (Patent document 4, Ex. 15-11), trans-[4-({[3-({[3-chloro-5-(trifluoromethyl)benzyl](1-methyl-1H-pyrazol-3-yl)amino}methyl)-5-(trifluoromethyl)pyridin-2-yl](ethyl)amino}methyl)cyclohexyl]acetic acid (Patent document 4, Ex. 15-12), trans-[4-({[3-({[3,5-bis(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetic acid (Patent document 4, Ex. 15-13), trans-[4-({[3-({[3-chloro-5-(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetic acid (Patent document 4, Ex. 15-14), trans-[4-({[3-({[3,5-bis(trifluoromethyl)benzyl](2-methyl-2H-tetrazol-5-yl)amino}methyl)-5-bromopyridin-2-yl](ethyl)amino}methyl)cyclohexyl]acetic acid (Patent document 4, Ex. 16-1), trans-[4-({[3-({[3,5-bis(trifluoromethyl)benzyl](2-methyl-2H-tetrazol-5-yl)amino}methyl)-5-phenylpyridin-2-yl](ethyl)amino}methyl)cyclohexyl]acetic acid (Patent document 4, Ex. 16-2), trans-[4-({[5-({[3,5-bis(trifluoromethyl)benzyl](2-methyl-2H-tetrazol-5-yl)

amino}methyl)-3,3'-bipyridin-6-yl](ethyl)amino}methyl) cyclohexyl]acetic acid (Patent document 4, Ex. 16-3), trans-[4-({[3-({[3,5-bis(trifluoromethyl)benzyl](2-methyl-2H-tetrazol-5-yl)amino}methyl)quinolin-2-yl](ethyl) amino}methyl)cyclohexyl]acetic acid (Patent document 5, Ex. 4), trans-[4-({[3-({[3,5-bis(trifluoromethyl)benzyl](2-methyl-2H-tetrazol-5-yl)amino}methyl)-6,7-difluoroquinolin-2-yl](ethyl)amino}methyl)cyclohexyl]acetic acid (Patent document 5, Ex. 5-1), ethyl trans-(4-{[{2-[({1-[3,5-bis(trifluoromethyl)phenyl]ethyl}{5-[2-(methylthio)ethoxy]pyrimidin-2-yl}amino)methyl]-4-(trifluoromethyl)phenyl} (ethyl)amino]methyl}cyclohexyl)acetate (Patent document 6, Example 43), trans-(4-{[{2-[({1-[3,5-bis(trifluoromethyl) phenyl]ethyl}{5-[2-(methylthio)ethoxy]pyrimidin-2-yl}amino)methyl]-4-(trifluoromethyl)phenyl}(ethyl)amino] methyl}cyclohexyl)acetic acid (Patent document 6, Example 44), trans-(4-{[{2-[({1-[3,5-bis(trifluoromethyl)phenyl] ethyl}{5-[2-(methylsulfonyl)ethoxy]pyrimidin-2-yl}amino) methyl]-4-(trifluoromethyl)phenyl}(ethyl)amino] methyl}cyclohexyl)acetic acid (Patent document 6, Example 45), and the like, but the esters are not limited to these examples.

Compounds represented by the aforementioned general formula (6) for preparing the specific compounds mentioned above are also preferred.

Among them, those compounds in which $R^1$ in the general formula (1) is methyl group are preferred. More specifically, examples include, for example, trans-[4-({[6-({[3,5-bis(trifluoromethyl)benzyl](2-methyl-2H-tetrazol-5-yl) amino}methyl)indan-5-yl](ethyl)amino}methyl)cyclohexyl]acetic acid hydrochloride (Patent document 1, Example 111), trans-[4-({[2-({[3,5-bis(trifluoromethyl)benzyl](2-methyl-2H-tetrazol-5-yl)amino}methyl)-4-(trifluoromethoxy)phenyl](ethyl)amino}methyl)cyclohexyl]acetic acid hydrochloride (Patent document 1, Example 115), trans-[4-({[2-({[3,5-bis(trifluoromethyl)benzyl](2-methyl-2H-tetrazol-5-yl)amino}methyl)-4-(trifluoromethyl)phenyl](ethyl) amino}methyl)cyclohexyl]acetic acid hydrochloride (Patent document 1, Example 118), trans-[4-({[6-({[3,5-bis(trifluoromethyl)benzyl](2-methyl-2H-tetrazol-5-yl) amino}methyl)-2,2-difluoro-1,3-benzodioxol-5-yl](ethyl) amino}methyl)cyclohexyl]acetic acid hydrochloride (Patent document 1, Example 134), trans-[4-({[7-({[3,5-bis(trifluoromethyl)benzyl](2-methyl-2H-tetrazol-5-yl) amino}methyl)-2,2,3,3-tetrafluoro-2,3-dihydro-1,4-benzodioxin-6-yl](ethyl)amino}methyl)cyclohexyl]acetic acid hydrochloride (Patent document 1, Example 137), trans-[4-({[2-({[3,5-bis(trifluoromethyl)benzyl](2-methyl-2H-tetrazol-5-yl)amino}methyl)-5-methyl-4-(trifluoromethyl)phenyl](ethyl)amino}methyl)cyclohexyl]acetic acid hydrochloride (Patent document 1, Example 142), trans-[4-({[2-({[3,5-bis(trifluoromethyl)benzyl](2-methyl-2H-tetrazol-5-yl)amino}methyl)-4-methyl-5-(trifluoromethyl)phenyl](ethyl)amino}methyl)cyclohexyl]acetic acid hydrochloride (Patent document 1, Example 143), trans-[4-({[2-({[3,5-bis(trifluoromethyl)benzyl](2-methyl-2H-tetrazol-5-yl)amino}methyl)-4-bromophenyl](ethyl) amino}methyl)cyclohexyl]acetic acid hydrochloride (Patent document 1, Example 147), trans-[4-({[2-({[3,5-bis(trifluoromethyl)benzyl](2-methyl-2H-tetrazol-5-yl) amino}methyl)-4,5-dimethylphenyl](ethyl)amino}methyl) cyclohexyl]acetic acid hydrochloride (Patent document 1, Example 151), trans-[4-({[2-({[3,5-bis(trifluoromethyl)benzyl](2-methyl-2H-tetrazol-5-yl)amino}methyl)-4-(trifluoromethylthio)phenyl](ethyl)amino}methyl)cyclohexyl]acetic acid hydrochloride (Patent document 1, Example 152), trans-[4-({[2-({[3,5-bis(trifluoromethyl)benzyl](2-methyl-2H-tetrazol-5-yl)amino}methyl)-4-chloro-5-ethylphenyl](ethyl)amino}methyl)cyclohexyl]acetic acid hydrochloride (Patent document 1, Example 153), trans-[4-({[2-({[3,5-bis(trifluoromethyl)benzyl](2-methyl-2H-tetrazol-5-yl) amino}methyl)-5-methoxy-4-methylphenyl](ethyl) amino}methyl)cyclohexyl]acetic acid hydrochloride (Patent document 1, Example 155), trans-[4-({[2-({[3,5-bis(trifluoromethyl)benzyl](p-tolyl)amino}methyl)-4-(trifluoromethoxy)phenyl](ethyl)amino}methyl)cyclohexyl]acetic acid dihydrochloride (Patent document 1, Example 162), trans-[4-({[2-({[3,5-bis(trifluoromethyl)benzyl](5-methyl-[1,2,4]oxadiazol-3-yl)amino}methyl)-4-(trifluoromethoxy) phenyl](ethyl)amino}methyl)cyclohexyl]acetic acid hydrochloride (Patent document 1, Example 163), trans-[4-({[2-({[3,5-bis(trifluoromethyl)benzyl](5-methyl-[1,2,4]oxadiazol-3-yl)amino}methyl)-5-methyl-4-(trifluoromethyl)phenyl](ethyl)amino}methyl)cyclohexyl]acetic acid hydrochloride (Patent document 1, Example 164), trans-[4-({[2-({[3,5-bis(trifluoromethyl)benzyl](2-methyl-2H-tetrazol-5-yl) amino}methyl)-4-methyl-5-(trifluoromethyl)phenyl](ethyl) amino}methyl)cyclohexyl]acetic acid (Patent document 1, Example 167), trans-[4-({[2-({[3,5-bis(trifluoromethyl)benzyl](2-methyl-2H-tetrazol-5-yl)amino}methyl)-5-methyl-4-(trifluoromethyl)phenyl](ethyl)amino}methyl)cyclohexyl] acetic acid methanesulfonate (Patent document 1, Example 168), ethyl trans-[4-({[2-({[3,5-bis(trifluoromethyl)benzyl] (2-methyl-2H-tetrazol-5-yl)amino}methyl)-5-methyl-4-(trifluoromethyl)phenyl](ethyl)amino}methyl)cyclohexyl]acetate (Patent document 1, Example 169), trans-[4-({[2-({[3, 5-bis(trifluoromethyl)benzyl](2-methyl-2H-tetrazol-5-yl) amino}methyl)-5-methyl-4-(trifluoromethyl)phenyl](ethyl) amino}methyl)cyclohexyl]acetic acid (Patent document 1, Example 170), trans-[4-({[2-({[3-methyl-5-(trifluoromethyl)benzyl](2-methyl-2H-tetrazol-5-yl)amino}methyl)-5-methyl-4-(trifluoromethyl)phenyl](ethyl)amino}methyl)cyclohexyl]acetic acid (Patent document 1, Example 171), trans-[4-({[2-({[3-methyl-5-(trifluoromethyl)benzyl](5-methyl-[1,2,4]oxadiazol-3-yl)amino}methyl)-5-methyl-4-(trifluoromethyl)phenyl](ethyl)amino}methyl)cyclohexyl]acetic acid (Patent document 1, Example 172), ethyl trans-[4-({[2-({(4S,5R)-5-[3,5-bis(trifluoromethyl) phenyl]-4-methyl-2-oxo-1,3-oxazolidin-3-yl}methyl)-4-(trifluoromethoxy)phenyl](ethyl)amino}methyl)cyclohexyl] acetate (Patent document 2, Ex. 11), trans-[4-({[2-({(4S,5R)-5-[3,5-bis(trifluoromethyl)phenyl]-4-methyl-2-oxo-1,3-oxazolidin-3-yl}methyl)-4-(trifluoromethyl)benzyl](ethyl) amino}methyl)cyclohexyl]acetic acid (Patent document 2, Ex. 13), ethyl trans-[4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino}methyl)cyclohexyl]acetate (Patent document 2, Ex. 34), trans-[4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino}methyl)cyclohexyl]acetic acid (Patent document 2, Ex. 64), trans-[4-({[2-({(4S,5R)-5-[3,5-bis(trifluoromethyl)phenyl]-4-methyl-2-oxo-1,3-oxazolidin-3-yl}methyl)pyridin-3-yl](ethyl)amino}methyl)cyclohexyl] acetic acid (Patent document 2, Ex. 69), trans-[4-({[2-({(4S, 5R)-5-[3,5-bis(trifluoromethyl)phenyl]-4-methyl-2-oxo-1, 3-oxazolidin-3-yl}methyl)-6-isopropenylpyridin-3-yl] (ethyl)amino}methyl)cyclohexyl]acetic acid (Patent document 2, Ex. 70), trans-[4-({[2-({(4S,5R)-5-[3,5-bis(trifluoromethyl)phenyl]-4-methyl-2-oxo-1,3-oxazolidin-3-yl}methyl)-6-isopropylpyridin-3-yl](ethyl)amino}methyl) cyclohexyl]acetic acid (Patent document 2, Ex. 71), trans-[4-

({[2-({(4S,5R)-5-[3,5-bis(trifluoromethyl)phenyl]-4-methyl-2-oxo-1,3-oxazolidin-3-yl}methyl)-6-cyclopropylpyridin-3-yl](ethyl)amino}methyl)cyclohexyl] acetic acid (Patent document 2, Ex. 72), trans-[4-({[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino}methyl)cyclohexyl]acetic acid (Patent document 2, Ex. 73), trans-[4-({[2-({[3,5-bis(trifluoromethyl)benzyl)][5-(2-hydroxyethoxy)pyrimidin-2-yl]amino}methyl)-4-(trifluoromethyl)phenyl](ethyl)amino}methyl)cyclohexyl]acetic acid (Patent document 3, Ex. 13), trans-[4-({[2-({[3,5-bis(trifluoromethyl)benzyl](5-morpholinopyrimidin-2-yl)amino}methyl)-4-(trifluoromethyl)phenyl](ethyl)amino}methyl)cyclohexyl]acetic acid (Patent document 3, Ex. 57), ethyl trans-[4-({[3-({[3,5-bis(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-1), ethyl trans-[4-({ethyl[3-({(2-methyl-2H-tetrazol-5-yl)[3-nitro-5-(trifluoromethyl)benzyl]amino}methyl)-5-(trifluoromethyl)pyridin-2-yl]amino}methyl)cyclohexyl]acetate (Patent document 4, Ex. 5-2), ethyl trans-[4-({[3-({[3-cyano-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-3), ethyl trans-[4-({[3-({[3-chloro-2-fluoro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-4), ethyl trans-[4-({[3-({[3,5-bis(trifluoromethyl)benzyl](phenyl)amino}methyl)-5-(trifluoromethyl)pyridin-2-yl](ethyl)amino}methyl)cyclohexyl]acetate (Patent document 4, Ex. 5-5), ethyl trans-[4-({[3-({[3-chloro-5-(trifluoromethyl)benzyl](phenyl)amino}methyl)-5-(trifluoromethyl)pyridin-2-yl](ethyl)amino}methyl)cyclohexyl]acetate (Patent document 4, Ex. 5-6), ethyl trans-[4-({[3-({[3,5-bis(trifluoromethyl)benzyl](1-methyl-1H-pyrazol-3-yl)amino}methyl)-5-(trifluoromethyl)pyridin-2-yl](ethyl)amino}methyl)cyclohexyl]acetate (Patent document 4, Ex. 5-7), ethyl trans-[4-({[3-({[3-chloro-5-(trifluoromethyl)benzyl](1-methyl-1H-pyrazol-3-yl)amino}methyl)-5-(trifluoromethyl)pyridin-2-yl](ethyl)amino}methyl)cyclohexyl]acetate (Patent document 4, Ex. 5-8), ethyl trans-[4-({[3-({[3,5-bis(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetate (Patent document 4, Ex. 5-9), ethyl trans-[4-({[3-({[3-chloro-5-(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetate (Patent document 4, Ex. 5-10), ethyl trans-[4-({[3-({[3-chloro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetate (Patent document 4, Ex. 5-11), ethyl trans-[4-({[3-({[3,5-bis(trifluoromethyl)benzyl](methoxycarbonyl)amino}methyl)-5-(trifluoromethyl)pyridin-2-yl](ethyl)amino}methyl)cyclohexyl]acetate (Patent document 4, Ex. 6-1), ethyl trans-[4-({[3-({N-[3,5-bis(trifluoromethyl)benzyl]acetamido}methyl)-5-(trifluoromethyl)pyridin-2-yl](ethyl)amino}methyl)cyclohexyl]acetate (Patent document 4, Ex. 6-2), ethyl trans-[4-({[3-({1-[3,5-bis(trifluoromethyl)benzyl]-3,3-dimethylureido}methyl)-5-(trifluoromethyl)pyridin-2-yl](ethyl)amino}methyl)cyclohexyl]acetate (Patent document 4, Ex. 6-3), ethyl trans-[4-({[3-({N-[3,5-bis(trifluoromethyl)benzyl]methylsulfonamido}methyl)-5-(trifluoromethyl)pyridin-2-yl](ethyl)amino}methyl)cyclohexyl]acetate (Patent document 4, Ex. 6-4), ethyl trans-[4-({[3-({[3,5-bis(trifluoromethyl)benzyl](2-methyl-2H-tetrazol-5-yl)amino}methyl)-5-phenylpyridin-2-yl](ethyl)amino}methyl)cyclohexyl]acetate (Patent document 4, Ex. 7), ethyl trans-[4-({[5-({[3,5-bis(trifluoromethyl)benzyl](2-methyl-2H-tetrazol-5-yl)amino}methyl)-3,3'-bipyridin-6-yl](ethyl)amino}methyl)cyclohexyl]acetate (Patent document 4, Ex. 8-1), ethyl trans-[4-({[3-({[3,5-bis(trifluoromethyl)benzyl](2-methyl-2H-tetrazol-5-yl)amino}methyl)-5-chloropyridin-2-yl](ethyl)amino}methyl)cyclohexyl]acetate (Patent document 4, Ex. 13-1), ethyl trans-[4-({[3-({[3,5-bis(trifluoromethyl)benzyl](2-methyl-2H-tetrazol-5-yl)amino}methyl)-5-bromopyridin-2-yl](ethyl)amino}methyl)cyclohexyl]acetate (Patent document 4, Ex. 13-2), trans-[4-({[3-({[3,5-bis(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 14), trans-[4-({[3-({[3-chloro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 15-1), trans-[4-({ethyl[3-({(2-methyl-2H-tetrazol-5-yl)[3-nitro-5-(trifluoromethyl)benzyl]amino}methyl)-5-(trifluoromethyl)pyridin-2-yl]amino}methyl)cyclohexyl]acetic acid (Patent document 4, Ex. 15-2), trans-[4-({[3-({[3-cyano-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 15-3), trans-[4-({[3-({[3-chloro-2-fluoro-5-(trifluoromethyl)benzyl](2-methyl-2H-tetrazol-5-yl)amino}methyl)-5-(trifluoromethyl)pyridin-2-yl](ethyl)amino}methyl)cyclohexyl]acetic acid (Patent document 4, Ex. 15-4), trans-[4-({[3-({[3,5-bis(trifluoromethyl)benzyl](phenyl)amino}methyl)-5-(trifluoromethyl)pyridin-2-yl](ethyl)amino}methyl)cyclohexyl]acetic acid (Patent document 4, Ex. 15-5), trans-[4-({[3-({[3-chloro-5-(trifluoromethyl)benzyl](phenyl)amino}methyl)-5-(trifluoromethyl)pyridin-2-yl](ethyl)amino}methyl)cyclohexyl]acetic acid (Patent document 4, Ex. 15-6), trans-[4-({[3-({[3,5-bis(trifluoromethyl)benzyl](methoxycarbonyl)amino}methyl)-5-(trifluoromethyl)pyridin-2-yl](ethyl)amino}methyl)cyclohexyl]acetic acid (Patent document 4, Ex. 15-7), trans-[4-({[3-({N-[3,5-bis(trifluoromethyl)benzyl]acetamido}methyl)-5-(trifluoromethyl)pyridin-2-yl](ethyl)amino}methyl)cyclohexyl]acetic acid (Patent document 4, Ex. 15-8), trans-[4-({[3-({1-[3,5-bis(trifluoromethyl)benzyl]-3,3-dimethylureido}methyl)-5-(trifluoromethyl)pyridin-2-yl](ethyl)amino}methyl)cyclohexyl]acetic acid (Patent document 4, Ex. 15-9), trans-[4-({[3-({N-[3,5-bis(trifluoromethyl)benzyl]methylsulfonamido}methyl)-5-(trifluoromethyl)pyridin-2-yl](ethyl)amino}methyl)cyclohexyl]acetic acid (Patent document 4, Ex. 15-10), trans-[4-({[3-({[3,5-bis(trifluoromethyl)benzyl](1-methyl-1H-pyrazol-3-yl)amino}methyl)-5-(trifluoromethyl)pyridin-2-yl](ethyl)amino}methyl)cyclohexyl]acetic acid (Patent document 4, Ex. 15-11), trans-[4-({[3-({[3-chloro-5-(trifluoromethyl)benzyl](1-methyl-1H-pyrazol-3-yl)amino}methyl)-5-(trifluoromethyl)pyridin-2-yl](ethyl)amino}methyl)cyclohexyl]acetic acid (Patent document 4, Ex. 15-12), trans-[4-({[3-({[3,5-bis(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetic acid (Patent document 4, Ex. 15-13), trans-[4-({[3-({[3-chloro-5-(trifluoromethyl)benzyl](1-methyl-1H-1,2,4-triazol-3-yl)amino}methyl)-5-(trifluoromethyl)pyridin-2-yl](ethyl)amino}methyl)cyclohexyl]acetic acid (Patent document 4, Ex. 15-14), trans-[4-({[3-({[3,5-bis(trifluoromethyl)benzyl](2-methyl-2H-tetrazol-5-yl]amino}methyl)-5-bromopyridin-2-yl](ethyl)amino}methyl)cyclohexyl]acetic acid (Patent document 4, Ex. 16-1), trans-[4-({[3-({[3,5-bis(trifluoromethyl)benzyl](2-methyl-2H-tetrazol-5-yl)amino}methyl)-5-phenylpyridin-2-yl](ethyl)amino}methyl)cyclohexyl]acetic acid (Patent document 4, Ex. 16-2), trans-[4-({[5-({[3,5-bis(trifluoromethyl)benzyl](2-methyl-2H-tetrazol-5-yl)amino}methyl)-3,3'-bipyridin-6-yl](ethyl)amino}methyl)cyclohexyl]acetic acid (Patent document 4, Ex. 16-3), trans-[4-({[3-({[3,5-bis(trifluoromethyl)benzyl](2-methyl-2H-tetrazol-5-yl)amino}methyl)quinolin-2-yl](ethyl)amino}methyl)cyclohexyl]acetic acid (Patent document 5, Ex. 4), trans-[4-({[3-({[3,5-bis(trifluoromethyl)benzyl](2-methyl-2H-tetrazol-5-yl)amino}methyl)-6,7-difluoroquinolin-2-yl](ethyl)amino}methyl)cyclohexyl]acetic acid (Patent document 5, Ex. 5-1), ethyl trans-(4-{[{2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino]methyl}cyclohexyl)acetate (Patent document 6, Example 43), trans-(4-{[{2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino]methyl}cyclohexyl)acetic acid (Patent document 6, Example 44), trans-(4-{[{2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino]methyl}cyclohexyl)acetic acid (Patent document 6, Example 45), and the like, but the esters are not limited to these examples.

Compounds represented by the aforementioned general formula (6) for preparing the specific compounds mentioned above are also preferred.

In the method of the present invention, trans-{4-[(alkylamino)methyl]-cyclohexyl}acetic acid esters represented by the aforementioned general formula (1) (in the formula, $R^1$ and $R^2$ have the same meanings as those defined above) can be prepared from tranexamic acid by the following steps:
(a) the step of acylating tranexamic acid (2) to prepare a compound represented by the aforementioned general formula (3) ($R^1$ in the formula has the same meaning as that defined above);
(b) the step of reacting the compound represented by the aforementioned general formula (3) ($R^1$ in the formula has the same meaning as that defined above) obtained in the aforementioned step (a) with a halogenating agent or an active esterifying agent to prepare a compound represented by the aforementioned general formula (4) ($R^1$ in the formula has the same meaning as that defined above, and X represents a halogen atom or an active ester residue);
(c) the step of reacting the compound represented by the aforementioned general formula (4) obtained in the aforementioned step (b) with diazomethane or trimethylsilyldiazomethane to prepare a compound represented by the aforementioned general formula (5) ($R^1$ in the formula has the same meaning as that defined above);
(d) the step of reacting the compound represented by the aforementioned general formula (5) ($R^1$ in the formula has the same meaning as that defined above) obtained in the aforementioned step (c) with an alcohol compound represented as $R^2$—OH ($R^2$ in the formula has the same meaning as that defined above) in the presence of a silver salt and a tertiary amine to prepare a compound represented by the aforementioned general formula (6) ($R^1$ and $R^2$ in the formula have the same meanings as those defined above); and
(e) the step of reducing amide group of the compound represented by the aforementioned general formula (6) ($R^1$ and $R^2$ in the formula have the same meanings as those defined above) obtained in the aforementioned step (d).

The step (a) is for subjecting tranexamic acid (2) to an acylation reaction to prepare the amide compound (3).

The acylation can be performed, for example, in an acid anhydride in the presence of a catalytic amount of sulfuric acid. As the acid anhydride, for example, symmetric acid anhydrides such as acetic anhydride, propionic anhydride, butanoic anhydride, pentanoic anhydride, and hexanoic anhydride, and mixed acid anhydrides such as acetic propionic anhydride, and acetic butanoic anhydride can be used. However, symmetric acid anhydrides are preferred, and acetic anhydride is particularly preferred. Although amount of the acid anhydride used is not particularly limited, the amount may be, for example, about 1.5 to 15.0-fold moles, preferably about 8.0 to 10.0-fold moles based on tranexamic acid (2).

Although this reaction can be performed in the presence or absence of a solvent, the reaction is desirably performed without solvent. Reaction temperature is usually in the range of −20 to 100° C., preferably 0 to 50° C. Reaction time is usually preferably 5 minutes to 24 hours, more preferably 10 minutes to 15 hours.

As for this reaction, the target amide compound (3) can also be prepared by performing a similar reaction using an acid halide such as acetyl chloride, acetyl bromide, propionyl chloride, and butyryl chloride instead of the acid anhydride.

The step (b) is for converting the carboxyl group of the amide compound (3) to the acyl derivative (4) with a high eliminating ability by using a halogenating agent or an active esterifying agent.

Examples of the halogenating agent used for this reaction include, for example, oxalyl chloride, thionyl chloride, thionyl bromide, carbon tetrachloride and triphenylphosphine, carbon tetrabromide and triphenylphosphine, cyanuric chloride and triethylamine, and the like, and thionyl chloride can be preferably used. The active esterifying agent may be, for example, a combination of a phenol such as pentafluorophenol and p-nitrophenol and a condensing agent such as DCC and WSC, as well as a combination of triethylamine and ethyl chlorocarbonate, isobutyl chlorocarbonate, trifluoroacetyl chloride, trichloroacetyl chloride, or the like. Although amount of the halogenating agent or the active esterifying agent used is not particularly limited, the amount may be, for example, about 1.0 to 50.0-fold moles, preferably about 1.5 to 10.0-fold moles, of the carboxylic acid compound (3).

Although this reaction can be performed in the presence or absence of a solvent, the reaction is preferably performed in a solvent. The solvent to be used is not particularly limited so long as a solvent inert to the reaction is chosen. Examples include, for example, aromatic hydrocarbon type solvents such as benzene, toluene, xylene, mesitylene, chlorobenzene, 1,2-dichlorobenzene and nitrobenzene, aliphatic hydrocarbon type solvents such as n-hexane, cyclohexane, n-octane and n-decane, halogenated hydrocarbon type solvents such as methylene chloride, 1,2-dichloroethane, chloroform and carbon tetrachloride, ether type solvents such as diethyl ether, tetrahydrofuran, 1,4-dioxane, 1,3-dioxane, t-butyl methyl ether, monoglyme and diglyme, acetonitrile, acetone, and the like. Among them, aromatic hydrocarbon type solvents such as benzene, toluene, xylene, mesitylene, chlorobenzene, 1,2-dichlorobenzene and nitrobenzene are preferred, and benzene and toluene are particularly preferred. These solvents may be used independently, or arbitrary two or more kinds of these solvents can also be used in combination. Amount of the solvent used is not particularly limited.

Reaction temperature is usually in the range of −30 to 120° C., preferably 0 to 50° C. Reaction time is usually preferably 1 to 36 hours, more preferably 3 to 15 hours.

The step (c) is for reacting the compound (4) and diazomethane or trimethylsilyldiazomethane to prepare the diazoketone compound (5).

Amount of diazomethane or trimethylsilyldiazomethane used in this reaction is, for example, about 1.0 to 10.0-fold moles, more preferably about 1.5 to 5.0-fold moles, of the compound (4).

This reaction is preferably performed in a solvent. Examples of the solvent to be used include, for example, ether type solvents such as diethyl ether, tetrahydrofuran, 1,4-dioxane, 1,3-dioxane, t-butyl methyl ether, monoglyme and diglyme, halogenated hydrocarbon type solvents such as methylene chloride, 1,2-dichloroethane, chloroform and carbon tetrachloride, acetonitrile, and the like. Among them, ether type solvents such as diethyl ether, tetrahydrofuran, 1,4-dioxane, 1,3-dioxane, t-butyl methyl ether, monoglyme and diglyme, and acetonitrile are preferred, and a combination of tetrahydrofuran and acetonitrile is particularly preferred.

Reaction temperature is usually in the range of −35 to 30° C., preferably −20 to 20° C. Reaction time is usually preferably 1 to 12 hours, more preferably 2 to 8 hours.

The step (d) is for reacting the diazoketone compound (5) with an alcohol compound in the presence of a silver salt and a tertiary amine to prepare the compound (6), in which the carbon number is increased by 1, according to the Arndt-Eistert reaction.

By variously changing the alcohol compound used in this reaction, variety of trans-{4-[(alkylamino)methyl] cyclohexyl}acetic acid esters (1) can be prepared. In the alcohol compound represented as $R^2$—OH, $R^2$ represents the aforementioned $C_{1-6}$ alkyl group, $C_{3-6}$ cycloalkyl group, ($C_{3-6}$ cycloalkyl)($C_{1-6}$ alkyl) group, $C_{6-10}$ aryl group, or $C_{7-12}$ aralkyl group. $R^2$ is preferably a $C_{1-6}$ alkyl group, and ethanol in which $R^2$ is ethyl group is more preferred. Although this reaction advances with an alcoholic solvent alone, an inert solvent such as ether type solvents may be used in combination. Examples of such a solvent include, for example, diethyl ether, tetrahydrofuran, 1,4-dioxane, and the like.

Examples of the silver salt to be used include, for example, silver oxide ($Ag_2O$), silver acetate ($AgOCOCH_3$), silver trifluoroacetate ($AgOCOCF_3$), silver trifluoromethanesulfonate ($AgOSO_2CF_3$), silver nitrate ($AgNO_3$), silver nitrite ($AgNO_2$), silver thiosulfate ($Ag_2S_2O_3$), silver carbonate ($Ag_2CO_3$), silver benzoate (AgOCOPh), and the like, and silver benzoate is preferred. Although amount of the silver salt used for this reaction is not particularly limited, the amount may be, for example, about 0.001 to 1.0-fold mole, preferably about 0.01 to 0.2-fold mole. As the tertiary amine to be used, for example, 4-methylmorpholine, triethylamine, and the like can be used, and triethylamine is preferred. Although amount of the tertiary amine used for this reaction is not particularly limited, the amount may be, for example, about 1.0 to 10.0-fold moles, preferably about 1.2 to 3.0-fold moles.

Reaction temperature is usually in the range of −20 to 120° C., preferably 20 to 80° C. Reaction time is usually preferably 1 minute to 12 hours, more preferably 5 minutes to 6 hours.

Step (e)

This step is for subjecting the amide compound (6) to reduction in order to prepare a trans-{4-[(alkylamino)methyl] cyclohexyl}acetic acid ester (1).

Examples of reducing agent include, for example, sodium borohydride, sodium cyanoborohydride, sodium triacetoxyborohydride, lithium borohydride, lithium aluminum hydride, borane complex, and the like, and sodium borohydride is preferred. Although amount of the reducing agent used is not particularly limited, the amount may be, for example, about 2 to 10-fold moles of the compound (6).

Examples of the solvent include, for example, methanol, ethanol, n-propanol, n-butanol, isopropanol, dichloromethane, chloroform, diethyl ether, tetrahydrofuran, 1,4-dioxane, monoglyme, diglyme, N,N-dimethylformamide, benzene, toluene, xylene, acetic acid, mixed solvents of these solvents, and the like. Acetic acid and tetrahydrofuran are preferred, and a combination of acetic acid and tetrahydrofuran is particularly preferred.

Reaction temperature is usually 0 to 140° C., preferably a temperature of from room temperature to around the boiling point of the solvent. Reaction time is usually 1 to 24 hours, preferably 3 to 12 hours.

EXAMPLES

The present invention will be more specifically explained with reference to examples. However, the scope of the present invention is not limited to the following example.

Example 1

Preparation of trans-{4-[(acetylamino)methyl] cyclohexyl}carboxylic acid

Tranexamic acid (10 g, 63.6 mmol) was suspended in acetic anhydride (50 mL), this suspension was added with concentrated sulfuric acid (0.01 mL) at room temperature, and the mixture was stirred overnight at the same temperature. Under ice cooling, the reaction mixture was added with water (100 mL), and the mixture was stirred at room temperature for 1 hour to decompose excess acetic anhydride. The reaction solution was concentrated under reduced pressure, and the residue was further azeotroped with toluene. The resulting precipitates were collected by filtration, washed with ether, and dried under reduced pressure to obtain trans-{4-[(acetylamino) methyl]cyclohexyl}carboxylic acid as white solid (12.46 g, 98%).

Example 2

Preparation of ethyl trans-{4-[(acetylamino)methyl] cyclohexyl}acetate

A suspension of trans-{4-[(acetylamino)] cyclohexyl}carboxylic acid (2.0 g, 10.0 mmol) in toluene (10 mL) was added with thionyl chloride (2.38 g, 20.0 mmol), and the mixture was stirred at room temperature for 12 hours, and evaporated under reduced pressure. The residue was dissolved in a mixture of tetrahydrofuran and acetonitrile (1:1, 15 mL), the solution was added with a solution of trimethylsilyldiazomethane (2 M solution in ether, 10.0 mL, 20.0 mmol) in a mixture of tetrahydrofuran and acetonitrile (1:1, 15 mL) under cooling at −15° C., and the mixture was stirred at 0° C. for 4 hours. The reaction solution was diluted with 5% aqueous citric acid (50 mL), and extracted with chloroform (50 mL). The organic layer was washed successively with saturated aqueous sodium hydrogencarbonate and saturated brine, dried over anhydrous sodium sulfate, and concentrated under reduced pressure to obtain a diazoketone compound (5) as pale yellow crystals (2.28 g).

The resulting diazoketone compound was dissolved in ethanol (20 mL), the solution was added dropwise with a solution of silver benzoate (114.5 mg, 0.50 mmol) in triethylamine (2.20 g, 20.0 mmol) with stirring at 50° C., and the mixture was stirred for 15 minutes. The reaction solution was left to cool, and then added with saturated aqueous sodium hydrogencarbonate (50 mL), and the mixture was extracted with ethyl acetate (80 mL). The organic layer was washed successively with 5% aqueous citric acid and saturated brine, dried over anhydrous sodium sulfate and concentrated under reduced pressure. The resulting residue was purified by silica gel chromatography (acetone/hexane=6%→66%) to obtain ethyl trans-{4-[(acetylamino)methyl]cyclohexyl}acetate as white solid (1.19 g, 49% for three steps).

This was recrystallized from hexane and acetone to obtain colorless needles.

IR (ATR) cm$^{-1}$: 3301, 2912, 2849, 1724, 1644, 1557, 1448, 1418, 1376, 1303, 1282, 1236, 1219, 1199, 1176, 1146, 1134, 1037, 747

$^1$H-NMR (400 MHz, CDCl$_3$) δ: 0.93-1.04 (4H, m), 1.25 (3H, t, J=7.2 Hz), 1.41-1.43 (1H, m), 1.72-1.80 (5H, m), 1.98 (3H, s), 2.18 (2H, d, J=7.2 Hz), 3.10 (2H, t, J=6.4 Hz), 4.12 (2H, q, J=7.2 Hz), 5.49 (1H, br-s)

mp: 74-76° C.

Elemental analysis for C$_{13}$H$_{23}$NO$_3$:

Calculated: C, 64.70; H, 9.61; N, 5.80.

Found: C, 64.69; H, 9.47; N, 5.84.

Example 3

Preparation of ethyl trans-{4-[(ethylamino)methyl]cyclohexyl}acetate

Ethyl trans-{4-[(acetylamino)methyl]cyclohexyl}acetate (1.19 g, 4.93 mmol) was dissolved in tetrahydrofuran (25 mL), the solution was added with sodium borohydride (932 mg, 24.66 mmol), the mixture was added dropwise with a solution of acetic acid (1.48 g, 24.66 mmol) in tetrahydrofuran (25 mL) over 1 hour under reflux by heating, and the mixture was stirred at the same temperature for 6 hours. The reaction mixture was added dropwise with water with stirring under ice cooling, and the reaction was thereby quenched. The reaction mixture was made alkaline with 2 M aqueous sodium hydroxide, and extracted with ethyl acetate, and the organic layer was successively washed with water and saturated brine, and dried over anhydrous sodium sulfate. The solvent was evaporated under reduced pressure, the resulting crude product of ethyl trans-{4-[(ethylamino)methyl]cyclohexyl}acetate was dissolved in ethanol (20 mL), the solution was added with 4 M hydrochloric acid in ethyl acetate (6 mL), and the mixture was stirred for 12 hours. The reaction mixture was diluted with ethyl acetate, and the organic layer was successively washed with 2 M sodium hydroxide, water, and saturated brine, and dried over anhydrous sodium sulfate. The solvent was evaporated under reduced pressure to obtain the objective ethyl trans-{4-[(ethylamino)methyl]cyclohexyl}acetate as pale brown oil (1.12 g, 99%).

As described above, ethyl trans-{4-[(ethylamino)methyl]cyclohexyl}acetate could be prepared from tranexamic acid by the preparation method of the present invention at a total yield of 47.5%. The preparation method of the present invention gave a higher yield than that of the known method described in the reference (yield being 32.2% in Patent document 1), and no step for separating isomers was necessary attributable to the use of the inexpensive tranexamic acid as the starting material. Therefore, the method is an extremely superior method for efficiently preparing a trans-{4-[(alkylamino)methyl]cyclohexyl}acetic acid ester.

INDUSTRIAL APPLICABILITY

According to the method of the present invention, a trans-{4-[(alkylamino)methyl]cyclohexyl}acetic acid ester, which is useful as a reagent or a raw material compound for manufacture of medicaments, agricultural chemicals, industrial products and the like, can be efficiently prepared in a high yield from an inexpensive raw material compound. This method is especially advantageous for reducing manufacturing cost and improving manufacturing efficiency from an industrial viewpoint.

What is claimed is:

1. A method for preparing a trans-{4-[(alkylamino)methyl]cyclohexyl}acetic acid ester represented by the following general formula (1):

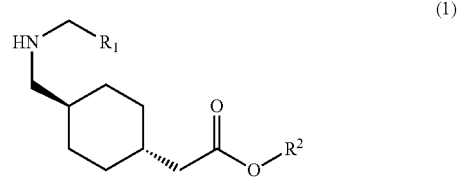

(1)

wherein R$^1$ represents a hydrogen atom or a C$_{1-6}$ alkyl group, and R$^2$ represents a C$_{1-6}$ alkyl group, a C$_{3-6}$ cycloalkyl group, a (C$_{3-6}$ cycloalkyl)(C$_{1-6}$ alkyl) group, a C$_{6-10}$ aryl group, or a C$_{7-12}$ aralkyl group, which comprises reducing the amide group of a compound represented by the following general formula (6):

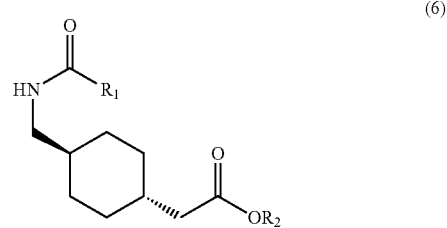

(6)

(R$^1$ and R$^2$ in the formula have the same meanings as those defined above).

2. The method according to claim 1, wherein sodium borohydride is used as a reducing agent.

3. The method according to claim 1, wherein R$^1$ is a methyl group.

4. A compound represented by the general formula (6) according to claim 1.

5. The compound according to claim 4, wherein R$^1$ is a methyl group.

6. The compound according to claim 4, which is used as an intermediate for preparation of a trans-{4-[(alkylamino)methyl]cyclohexyl}acetic acid ester represented by the general formula (1) (in the formula, R$^1$ represents a hydrogen atom or a C$_{1-6}$ alkyl group, and R$^2$ represents a C$_{1-6}$ alkyl group, a C$_{3-6}$ cycloalkyl group, a (C$_{3-6}$ cycloalkyl)(C$_{1-6}$ alkyl) group, a C$_{6-10}$ aryl group, or a C$_{7-12}$ aralkyl group).

7. A method for preparing the compound represented by the general formula (6) according to claim 4, which comprises reacting a compound represented by the following general formula (5):

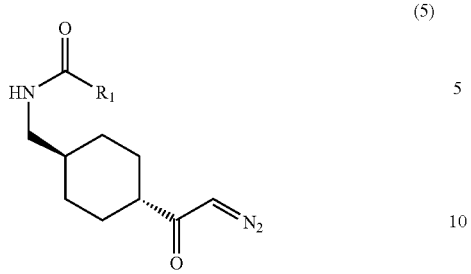

(5)

wherein R[1] represents a hydrogen atom or a $C_{1-6}$ alkyl group, with an alcohol compound represented as R[2]—OH wherein R[2] represents a $C_{1-6}$ alkyl group, a $C_{3-6}$ cycloalkyl group, a ($C_{3-6}$ cycloakyl)($C_{1-6}$ alkyl) group, a $C_{6-10}$ aryl group, or a $C_{7-12}$ aralkyl group, in the presence of a silver salt and a tertiary amine.

8. A method for preparing the compound represented by the general formula (6)

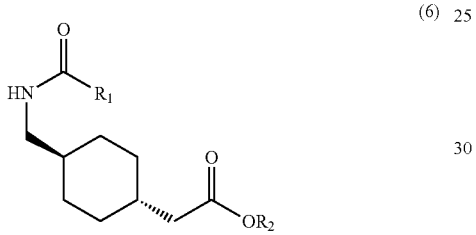

(6)

wherein R[1] represents a hydrogen atom or a $C_{1-6}$ alkyl group, and R[2] represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, which comprises reacting a compound represented by the following general formula (4):

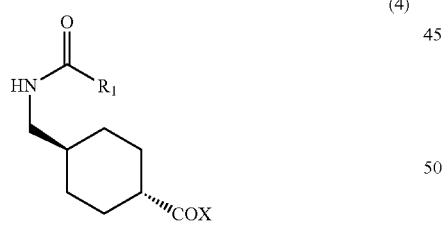

(4)

wherein R[1] represents a hydrogen atom or a $C_{1-6}$ alkyl group, and X represents a halogen atom or an active ester residue, with diazomethane or trimethylsilyldiazomethane to prepare a compound represented by the general formula (5) according to claim 7; and reacting the resulting compound represented by the general formula (5) with an alcohol compound represented as R[2]—OH wherein R[2] represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, in the presence of a silver salt and a tertiary amine.

9. A method for preparing the compound represented by the general formula (6)

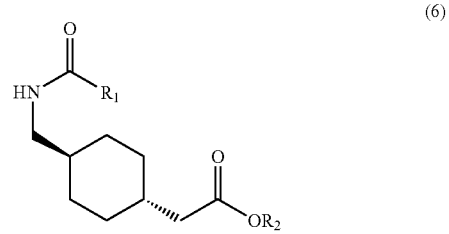

(6)

wherein R[1] represents a hydrogen atom or a $C_{1-6}$ alkyl group, and R[2] represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, which comprises reacting a compound represented by the following general formula (3):

[Formula 5]

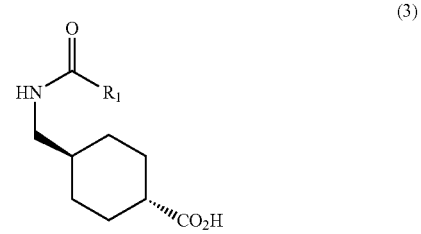

(3)

wherein R[1] represents a hydrogen atom or a $C_{1-6}$ alkyl group, with a halogenating agent or an active esterifying agent to prepare a compound represented by the general formula (4) according to claim 8; reacting the resulting compound represented by the general formula (4) with diazomethane or trimethylsilyldiazomethane to prepare a compound represented by the general formula (5)

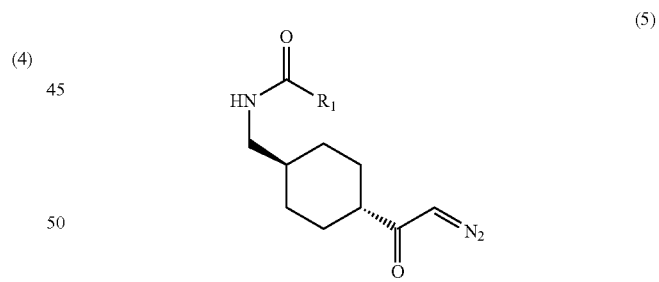

(5)

wherein R[1] represents a hydrogen atom or a $C_{1-6}$ alkyl group, and reacting the resulting compound represented by the general formula (5) with an alcohol compound represented as R[2]—OH wherein R[2] represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, in the presence of a silver salt and a tertiary amine.

10. A method for preparing the compound represented by the general formula (6)

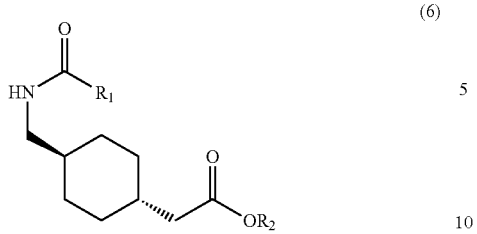

wherein $R^1$ represents a hydrogen atom or a $C_{1-6}$ alkyl group, and $R^2$ represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, which comprises acylating tranexamic acid to prepare a compound represented by the general formula (3) according to claim 9; reacting the resulting compound represented by the general formula (3) with a halogenating agent or an active esterifying agent to prepare a compound represented by the general formula (4)

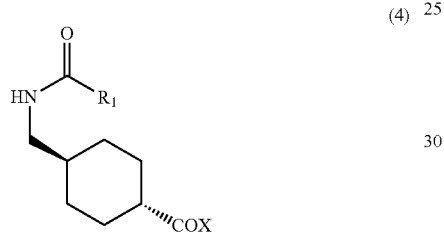

wherein $R^1$ represents a hydrogen atom or a $C_{1-6}$ alkyl group, and X represents a halogen atom or an active ester residue; reacting the resulting compound represented by the general formula (4) with diazomethane or trimethylsilyldiazomethane to prepare a compound represented by the general formula (5)

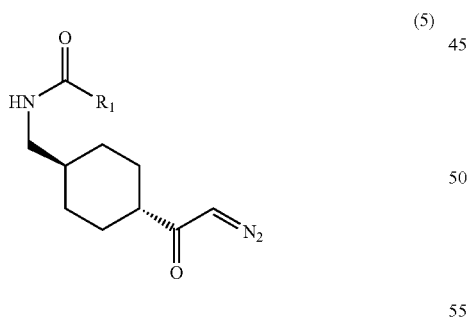

wherein $R^1$ represents a hydrogen atom or a $C_{1-6}$ alkyl group; and reacting the resulting compound represented by the general formula (5) with an alcohol compound represented as $R^2$—OH wherein $R^2$ represents a $C_{1-6}$ alkyl group, a $C_{3-6}$ cycloalkyl group, ($C_{3-6}$ cycloalkyl) ($C_{1-6}$ alkyl) group, a $C_{6-10}$ aryl group, or a $C_{7-12}$ aralkyl group, in the presence of a silver salt and a tertiary amine.

11. A method for preparing a trans-{4-[(alkylamino)methyl]cyclohexyl}acetic acid ester represented by the general formula (1)

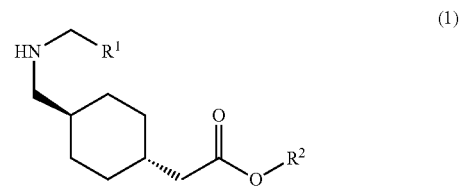

wherein $R^1$ represents a hydrogen atom or a $C_{1-6}$ alkyl group, and $R^2$ represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, which comprises:

(a) acylating tranexamic acid to prepare a compound represented by the general formula (3)

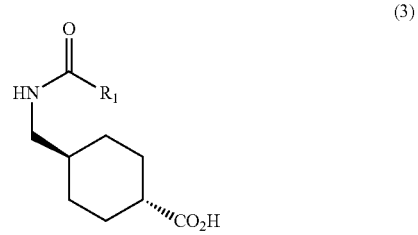

wherein $R^1$ represents a hydrogen atom or a $C_{1-6}$ alkyl group;

(b) reacting the compound represented by the general formula (3) obtained in the aforementioned step (a) with a halogenating agent or an active esterifying agent to prepare a compound represented by the general formula (4) according to claim 9;

(c) reacting the compound represented by the general formula (4) obtained in the aforementioned step (b) with diazomethane or trimethylsilyldiazomethane to prepare a compound represented by the general formula (5)

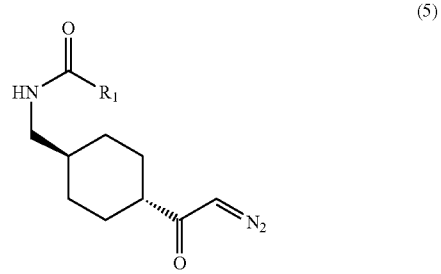

wherein $R^1$ represents a hydrogen atom or a $C_{1-6}$ alkyl group;

(d) reacting the compound represented by the general formula (5) obtained in the aforementioned step (c) with an alcohol compound represented as $R^2$—OH wherein $R^2$ represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, in the presence of a silver salt and a tertiary amine to prepare a compound represented by the general formula (6)

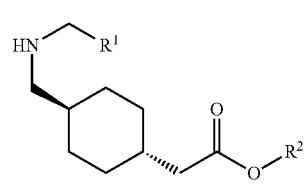

(6)

wherein R¹ represents a hydrogen atom or a $C_{1-6}$ alkyl group, and R² represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group; and (e) reducing the amide group of the compound represented by the general formula (6)

obtained in the aforementioned step (d).

12. A method for preparing a trans-{4-[(alkylamino)methyl]cyclohexyl}acetic acid ester represented by the general formula (1)

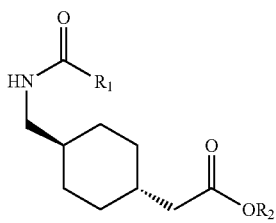

(1)

wherein R¹ represents a hydrogen atom or a $C_{1-6}$ alkyl group, and R² represents a $C_{1-6}$ alkyl group, a $C_{3-6}$ cycloalkyl group, a ($C_{3-6}$ cycloalkyl)($C_{1-6}$ alkyl) group, a $C_{6-10}$ aryl group, or a $C_{7-12}$ aralkyl group, which comprises one or more steps selected from the group consisting of the steps (a) to (e) according to claim 11.

13. The method according to claim 11, wherein R¹ of the general formula (1) is a methyl group.

\* \* \* \* \*